United States Patent [19]

Fuchs et al.

[11] 4,242,357
[45] Dec. 30, 1980

[54] CARBOXYLIC ACID ESTERS FOR COMBATING PESTS

[75] Inventors: Rainer A. Fuchs, Wuppertal; Ingeborg Hammann, Cologne; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 783,503

[22] Filed: Mar. 31, 1977

[30] Foreign Application Priority Data

Apr. 9, 1976 [DE] Fed. Rep. of Germany ....... 2615435
May 14, 1976 [DE] Fed. Rep. of Germany ....... 2621433

[51] Int. Cl.² .................. A01N 9/20; C07C 69/76; C07C 121/66; C07D 317/60
[52] U.S. Cl. .................... 424/282; 260/340.5 R; 260/465 D; 260/465 F; 424/304; 424/308; 424/309; 560/9; 560/20; 560/55; 560/105; 568/637
[58] Field of Search .................. 260/465 D, 340.5 R; 560/124, 105, 9, 55, 20; 424/304, 305, 308, 282

[56] References Cited

U.S. PATENT DOCUMENTS

| | | | |
|---|---|---|---|
| 3,666,789 | 5/1972 | Itaya et al. | 260/468 |
| 3,835,176 | 9/1974 | Matsuo et al. | 260/465 D |
| 3,968,124 | 7/1976 | Mizutani et al. | 260/340.5 |
| 3,973,036 | 8/1976 | Hipano et al. | 424/304 |
| 3,996,244 | 12/1976 | Fujimoto et al. | 560/105 X |
| 4,042,710 | 8/1977 | Bull et al. | 424/304 |
| 4,046,799 | 9/1977 | Kameswaran et al. | 260/465 D |

*Primary Examiner*—Dolph H. Torrence
*Attorney, Agent, or Firm*—Sprung, Felfe, Horn, Lynch & Kramer

[57] ABSTRACT

3-Phenoxybenzyl alcohols and carboxylic acid esters thereof for combating pests of the formula

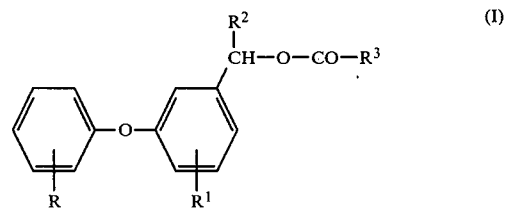

in which
R and R¹ are different and each represent hydrogen, fluorine or bromine,
R² represents cyano or ethynyl and
R³ represents the

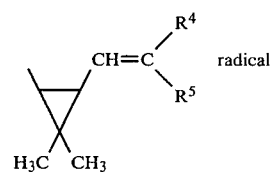

radical or the

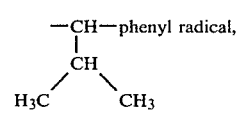

—CH—phenyl radical, wherein the phenyl ring can optionally carry one or more substituents selected independently from halogen, alkyl, alkylthio and alkoxy with in each case 1 to 4 carbon atoms, nitro and methylenedioxy, and
R⁴ and R⁵ are identical and each represent chlorine, bromine or methyl, and
R² represents hydrogen in case that
R³ represents the

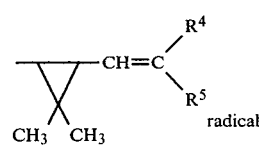

radical wherein
R⁴ and R⁵ are identical and each represent chlorine or bromine and
R³ represents the

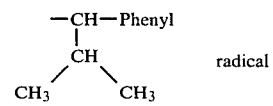

radical wherein the phenyl ring can carry the above mentioned substituents which possess insecticidal and acaricidal properties. The benzyl alcohols from which the esters are made are also new.

7 Claims, No Drawings

CARBOXYLIC ACID ESTERS FOR COMBATING PESTS

The present invention relates to and has for its objects the provision of particular new 3-phenoxybenzylalcohols and particularly to special carboxylic acid esters thereof which possess insecticidal and acaricidal properties, active compositions in the form of mixtures of such esters with solid and liquid dispersible carrier vehicles, and methods for producing such compounds and for using such esters in a new way especially for combating pests, e.g. insects and acarids, with other and further objects becoming apparent from a study of the within specification and accompanying examples.

It is known from German Published Specification DOS No. 2,335,347 and Belgian Patent Specification 801,946 that phenoxybenzyl-acetates or carboxylates, for example 3'-phenoxybenzyl-α-isopropyl-α-(3,4-dimethoxy- or 4-bromo- or 4-fluoro- or 3,4-dioxymethylenephenyl)-acetate and 3'-phenoxybenzyl-[2,2-dimethyl-3-(2,2-dichlorovinyl)-cyclopropane]-carboxylate possess insecticidal and acaricidal properties.

The present invention now provides, as new compounds, the substituted phenoxybenzyloxycarbonyl derivatives of the general formula

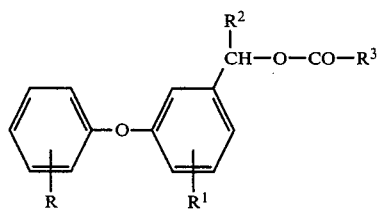

in which
R and $R^1$ are different and each represent hydrogen, fluorine or bromine,
$R^2$ represents cyano or ethynyl and
$R^3$ represents the

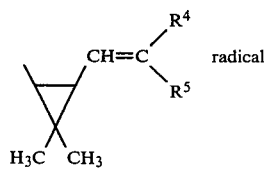

or the

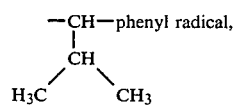

wherein the phenyl ring can optionally carry one or more substituents selected independently from halogen, alkyl, alkylthio and alkoxy with in each case 1 to 4 carbon atoms, nitro and methylenedioxy, and
$R^4$ and $R^5$ are identical and each represent chlorine, bromine or methyl, and
$R^2$ represents hydrogen in case that
$R^3$ represents the

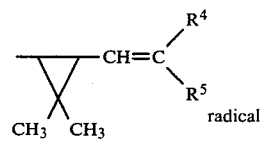

wherein
$R^4$ and $R^5$ are identical and each represent chlorine or bromine and
$R^3$ represents the

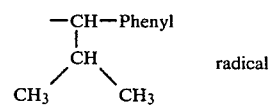

wherein the phenyl ring can carry the above mentioned substituents.

Preferably, R represents fluorine or bromine, $R^1$ represents hydrogen or fluorine, $R^2$ represents cyano or ethynyl and $R^3$ represents the 2,2-dimethyl-3-(2,2-dichloro- or 2,2-dibromo- or 2,2-dimethyl-vinyl)-cyclopropyl radical, or the α-isopropylbenzyl radical, the ring of which can optionally carry one or more substituents selected independently from fluorine, chlorine, bromine, methylenedioxy, methoxy, ethoxy, methylthio, ethylthio, straight-chain or branched alkyl with 1 to 3 carbon atoms and nitro and
$R^2$ represents hydrogen in case that
$R^3$ represents 2,2-dimethyl-3-(2,2-dichloro- or -2,2-dibromo-vinyl-)-cyclopropyl radical, or the α-isopropylbenzyl radical, the ring of which can optionally carry one or more substituents selected independently from fluorine, chlorine, bromine, methylendioxy, methoxy, ethoxy, methylthio, ethylthio, straight-chain or branched alkyl with 1 to 3 carbon atoms and/or nitro.

The general formula (I) includes the various possible stereo-isomers, the optical isomers and mixtures of these components.

Surprisingly, the substituted phenoxybenzyloxycarbonyl derivatives according to the invention exhibit a better insecticidal and acaricidal action than the corresponding previously known products of analogous structure and of the same type of action. The products according to the present invention thus represent a genuine enrichment of the art.

The present invention also provides a process for the preparation of a substituted phenoxybenzyloxycarbonyl derivative of the formula (I) in which a carbonyl halide of the general formula

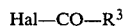   Hal—CO—$R^3$   (II), in which
$R^3$ has the above-mentioned meaning and
Hal represents halogen, preferably chlorine, is reacted with a substituted phenoxybenzyl alcohol of the general formula

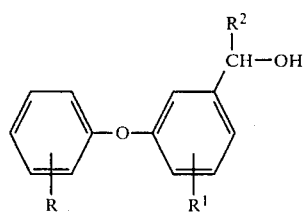

(III), in which R, $R^1$ and $R^2$ have the above-mentioned meanings, if appropriate in the presence of an acid acceptor and, if appropriate, in the presence of a solvent.

If for example, 3-(3-fluoro-phenoxy)-α-cyanobenzyl alcohol and α-isopropyl-4-ethoxyphenylacetic acid chloride are used as starting materials, the course of the reaction can be represented by the following equation:

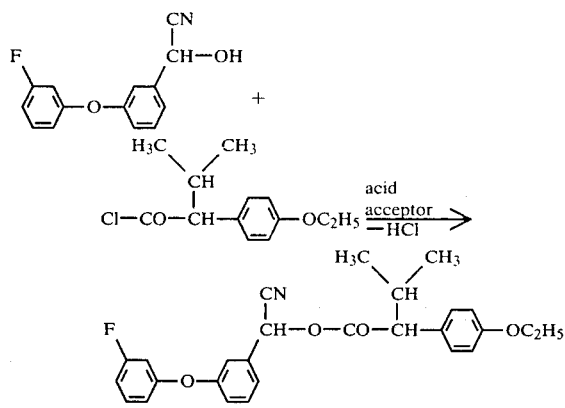

The carbonyl halides (II) to be used as starting materials are known and can be prepared in accordance with generally customary processes described in the literature for example, German Published Specifications DOS No. 2,365,555, 1,926,433 and 2,231,312.

The following may be mentioned as individual examples of these halides: 2,2-dimethyl-3-(2,2-dichlorovinyl)-cyclopropanecarboxylic acid chloride, 2,2-dimethyl-3-(2,2-dibromovinyl)-cyclopropanecarboxylic acid chloride, 2,2-dimethyl-3-(2,2-dimethylvinyl)-cyclopropanecarboxylic acid chloride, α-isopropyl-phenylacetic acid chloride, α-isopropyl-4-fluorophenylacetic acid chloride, α-isopropyl-4-chlorophenylacetic acid chloride, α-isopropyl-4-bromophenylacetic acid chloride, α-isopropyl-4-methylphenylacetic acid chloride, α-isopropyl-4-ethylphenylacetic acid chloride, α-isopropyl-4-n-propylphenylacetic acid chloride, α-isopropyl-4-isopropylphenylacetic acid chloride, α-isopropyl-4-methoxyphenylacetic acid chloride, α-isopropyl-4-ethoxyphenylacetic acid chloride, α-isopropyl-4-methylthiophenylacetic acid chloride, α-isopropyl-4-ethylthiophenylacetic acid chloride, α-isopropyl-4-nitrophenylacetic acid chloride, α-isopropyl-3-fluorophenylacetic acid chloride, α-isopropyl-3-bromophenylacetic acid chloride, α-isopropyl-3-chlorophenylacetic acid chloride, α-isopropyl-3-methylphenylacetic acid chloride, α-isopropyl-3-ethylphenylacetic acid chloride, α-isopropyl-3-methoxyphenylacetic acid chloride, α-isopropyl-3-ethoxyphenylacetic acid chloride, α-isopropyl-3-methylthiophenylacetic acid chloride, α-isopropyl-3-ethylthiophenylacetic acid chloride and α-isopropyl-3,4-methylenedioxyphenylacetic acid chloride.

The phenoxybenzyl alcohols (III), also to be used as starting compounds, have not hitherto been described in the literature. They are obtained by subjecting phenoxybenzaldehydes of the general formula

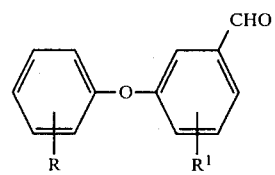

(IV), in which R and $R^1$ have the above-mentioned meanings,
(a), if $R^2$ is to represent hydrogen, to a reduction with a complex metal hydride in an inert solvent,
(b), if $R^2$ is to represent cyano, to a reaction with an alkali metal cyanide, for example sodium cyanide or potassium cyanide, in the presence of an acid, if appropriate with addition of a solvent, or
(c), if $R^2$ is to represent ethynyl, to a reaction with an ethynyl compound of the general formula $$HC\equiv C-MgHal \quad (V),$$

in which Hal represents halogen, preferably bromine, in a suitable solvent.

If, for example 3-(3-fluorophenoxy)-benzaldehyde and lithium aluminium hydride are used as starting materials according to process variant (a), 3-(2-fluorophenoxy)benzaldehyde and potassium cyanide are used as starting materials according to process variant (b) and 3-(4-bromophenoxy)-benzaldehyde and ethynylmagnesium bromide are used as starting materials according to process variant (c), the course of the reactions can be represented by the following equations:

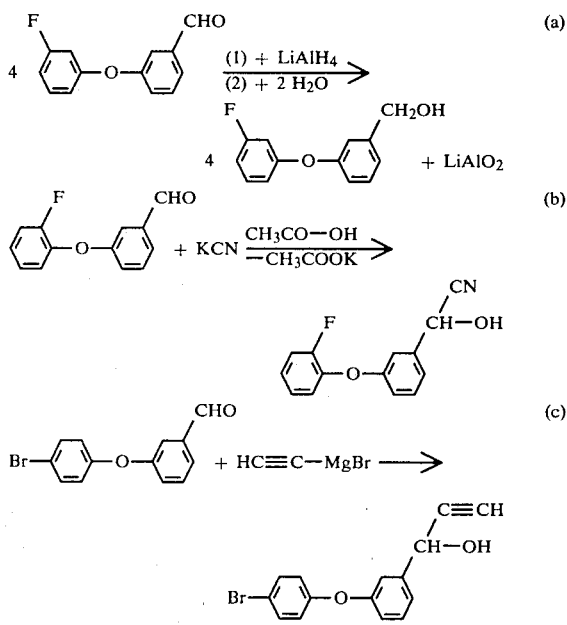

The ethynyl compounds of the formula (V) are described in the literature, as are the alkali metal cyanides and complex metal hydrides.

The phenoxy-benzaldehydes of the formula (IV) can be prepared in accordance with generally customary processes, in particular by, for example, reacting the corresponding phenoxybenzyl halides of the formula (VI) below, which are prepared in accordance with customary methods from the corresponding phenoxytoluenes, with hexamethylenetetramine in accordance with the following equation:

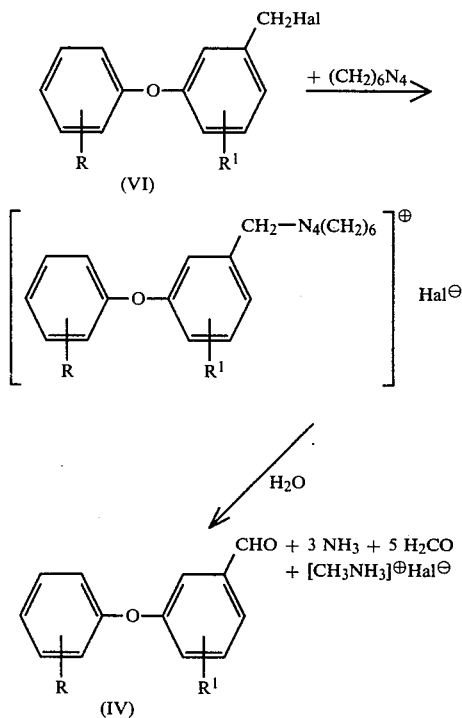

wherein
R and $R^1$ have the above-mentioned meanings and Hal represents halogen.

The following may be mentioned as individual examples of the phenoxybenzaldehydes (IV): 3-(4-fluorophenoxy)benzaldehyde, 3-(3-fluorophenoxy)-benzaldehyde, 3-(2-fluorophenoxy)-benzaldehyde, 3-(4-bromophenoxy)-benzaldehyde, 3-(3-bromophenoxy)-benzaldehyde and 3-(2-bromophenoxy)benzaldehyde.

The variants (a) to (c) for the preparation of the phenoxybenzaldehydes (IV) are preferably carried out in the presence of suitable solvents and diluents.

Ethers, such as diethyl ether, tetrahydrofuran and dioxane, as well as hydrocarbons, such as toluene and benzine, are especially suitable for carrying out process variant (a). When using sodium borohydride as a reducing agent, water, alcohols such as methanol and ethanol, and nitriles such as acetonitrile or propionitrile, can be used additionally. Water, alcohols such as methanol or ethanol, ethers such as diethyl ether and tetrahydrofuran, or nitriles such as acetonitrile, are especially suitable for carrying out process variant (b). Ethers, such as diethyl ether, tetrahydrofuran and dioxane, are especially suitable for process variant (c).

Lithium aluminum hydride and sodium borohydride are the preferred complex metal hydrides for use in process variant (a).

Acids which can be used in process variant (b) are inorganic acids, for example hydrochloric acid or sulfuric acid, or organic acids, for example acetic acid or formic acid.

In all of the process variants, the reaction temperature can be varied within a fairly wide range. In general, the reaction is carried out at $-10°$ to $110°$ C.; preferred temperatures are $0°$ to $60°$ C. for variant (a), $-5°$ to $20°$ C. for variant (b) and $0°$ to $80°$ C. for variant (c).

The reactions are in general allowed to take place under normal pressure.

To carry out process variant (a), the reactants are preferably employed in equimolar amounts. An excess of one or other component produces no advantage. In variant (b), the cyanide is preferably employed in 100–150% excess. In variant (c), the ethynyl compound is preferably employed in 20–50% excess. The reaction is preferably carried out in one of the above-mentioned solvents or diluents, at the stated temperatures, while stirring. After a reaction time of from one to several hours, in most cases at an elevated temperature, the reaction mixture is worked up in accordance with generally customary methods.

The compounds (IV) are obtained in the form of oils which can either be distilled or be freed from the last volatile constituents by so-called "slight distillation", that is to say by prolonged heating under reduced pressure to moderately elevated temperatures, and are purified in this way. They are characterized by the refractive index or boiling point.

The following may be mentioned as individual examples of the new phenoxybenzyl alcohols (III) which can be used for the preparation of the phenoxybenzyloxycarbonyl derivatives according to the invention: 3-(4-fluorophenoxy)benzyl alcohol, 3-(3-fluorophenoxy)-benzyl alcohol, 3-(4-bromophenoxy)-benzyl alcohol, 3-(3-bromophenoxy)-benzyl alcohol, 3-(2-fluorophenoxy)-benzyl alcohol, 3-(2-bromophenoxy)-benzyl alcohol, 3-(4-fluorophenoxy)-α-cyanobenzyl alcohol, 3-(3-fluorophenoxy)-α-cyanobenzyl alcohol, 3-(4-bromophenoxy)-α-cyanobenzyl alcohol, 3-(3-bromophenoxy)-α-cyanobenzyl alcohol, 3-(2-fluorophenoxy)-α-cyanobenzyl alcohol, 3-(2-bromophenoxy)-α-cyanobenzyl alcohol, 3-(4-fluorophenoxy)-α-ethynylbenzyl alcohol, 3-(3-fluorophenoxy)-α-ethynylbenzyl alcohol, 3-(4-bromophenoxy)-α-ethynylbenzyl alcohol, 3-(3-bromophenoxy)-α-ethynylbenzyl alcohol, 3-(2-fluorophenoxy)-α-ethynylbenzyl alcohol and 3-(2-bromophenoxy)-α-ethynylbenzyl alcohol.

All customary acid-binding agents can be used as acid acceptors for the preparation of the phenoxybenzyloxycarbonyl derivatives according to the invention. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between $0°$ and $100°$ C., preferably at $15°$ to $40°$ C.

The reaction is in general allowed to take place under normal pressure.

The process for the preparation of the compounds (I) according to the invention is preferably carried out in the presence of suitable solvents and diluents. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example, acetone, methyl ethyl ketone, methyl isopropyl ketone and methyl isobutyl ketone; and nitriles, such as acetonitrile and propionitrile.

To carry out the process, the starting compounds are preferably employed in equimolar amounts. An excess of one or the other reactant produces no worthwhile advantages. The reactants are in general brought together in one of the stated solvents and are in most cases stirred for one hour or more at an elevated temperature, to complete the reaction The reaction mixture is then poured into water and the organic phase is separated off and rinsed with water. After drying, the solvent is distilled off in vacuo.

The new compounds (I) are obtained in the form of oils, which in some cases cannot be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned, the substituted phenoxybenzyloxycarbonyl derivatives according to the present invention are distinguished by an excellent insecticidal and acaricidal activity.

The active compounds are well tolerated by plants, have a favorable level of toxicity to warm-blooded animals, and can be used for combating arthropod pests, especially insects and arachnids, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylliodes,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The compounds according to the invention exhibit powerful ectoparasiticidal and tickicidal properties, especially against ticks which, as animal ectoparasites, attack domesticated animals, such as, for example, cattle and sheep. At the same time, the active compounds according to the invention have a favorable level of toxicity to warm-blooded animals. They are therefore very suitable for combating animal ectoparasites, especially ticks.

The following may be mentioned as examples of economically important ectoparasites of this type, which play an important role particularly in tropical and subtropical countries; the Australian and South American one-host cattle tick *Boophilus microplus,* the South African cattle tick *Boophilus decoloratus,* both from the family of the Ixodidae, the African multi-host cattle ticks and sheep ticks, such as, for example, *Rhipicephalus appendiculatus, Rhipicephalus evertsi, Amblyomma hebraeum* and *Byalomma aruncatum* and the South American multi-host cattle ticks, such as, for example, *Amblyomma cajennense* and *Amblyomma americanum.*

In the course of time, such ticks have, in numerous areas, become resistant to the phosphoric acid esters and carbamates hitherto used as combating agents, so that the success in combating them is becoming increasingly questionable in many areas. To ensure economical stock-raising in the infested areas, there is an urgent need for agents by means of which all stages of development, that is to say larvae, metalarvae, nymphs, metanymphs and adults, even of resistant strains, for example of the genus Boophilus, can be combated reliably. For example, in Australia the Mackay strain, the Mouth Alfort strain and the Biarra strain of *Boophilus microplus* are highly resistant to the previously known phosphoric acid ester agents.

The active compounds according to the invention are equally active against both the normally sensitive and the resistant strains, for example of Boophilus. When applied in the usual manner to the host animal, they have a direct destructive effect on all forms parasitic on the animal, so that the cycle of development of the ticks is interrupted in the parasitic phase on the animal.

The laying of fertile eggs and hence the development and hatching of larvae is inhibited.

The agent may be used, for example, in a dip or bath, where the active compounds must remain stable for 6 months or more in the aqueous dip liquor, which becomes soiled and is exposed to microbial attack. Application may also be effected by spraying or pouring on.

In all use forms, the compounds according to the invention possess complete stability, that is to say no decrease in action is ascertainable after 6 months.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions. powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides and acaricides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0000001-100, preferably 0.01-10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present inventon contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples wherein the active compounds according to the present invention are each identified by the numbers recited in the preparative examples given later in the text and the known comparison compounds are identified as follows:

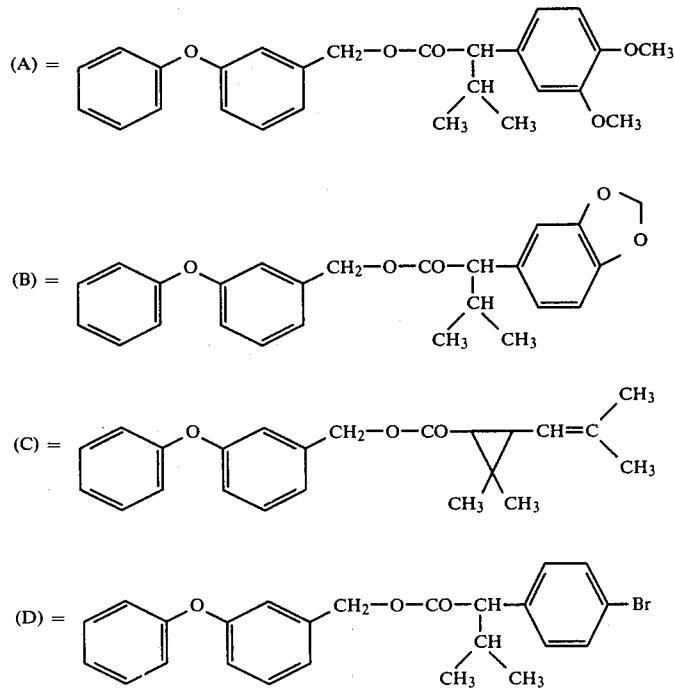

(E) = 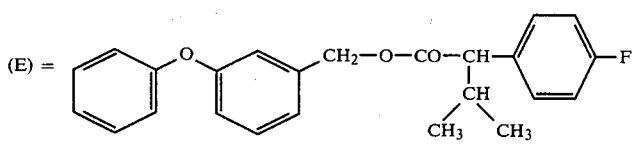

EXAMPLE 1

Myzus test (contact action)

Solvent: 3 parts by weight of acetone
Emulsifier: 1 part by weight of alkylaryl polyglcol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

TABLE 1

(insects which damage plants)
Myzus test

| Active compounds | Active compound concentration in % | Degree of destruction in % after 1 day |
|---|---|---|
| (A) | 0.1 | 100 |
|  | 0.01 | 90 |
|  | 0.001 | 0 |
| (B) | 0.1 | 100 |
|  | 0.01 | 95 |
|  | 0.001 | 0 |
| (C) | 0.1 | 100 |
|  | 0.01 | 100 |
|  | 0.001 | 0 |
| (5) | 0.1 | 100 |
|  | 0.01 | 100 |
|  | 0.001 | 95 |
| (11) | 0.1 | 100 |
|  | 0.01 | 100 |
|  | 0.001 | 95 |
| (3) | 0.1 | 100 |
|  | 0.01 | 100 |
|  | 0.001 | 100 |
| (14) | 0.1 | 100 |
|  | 0.01 | 100 |
|  | 0.001 | 100 |
| (12) | 0.1 | 100 |
|  | 0.01 | 100 |
|  | 0.001 | 80 |
| (4) | 0.1 | 100 |
|  | 0.01 | 100 |
|  | 0.001 | 95 |
| (16) | 0.1 | 100 |
|  | 0.01 | 100 |
|  | 0.001 | 99 |
| (10) | 0.1 | 100 |
|  | 0.01 | 100 |
|  | 0.001 | 100 |
| (6) | 0.1 | 100 |
|  | 0.01 | 100 |
|  | 0.001 | 100 |
| (7) | 0.1 | 100 |
|  | 0.01 | 100 |
|  | 0.001 | 100 |
| (15) | 0.1 | 100 |
|  | 0.01 | 100 |
|  | 0.001 | 100 |
| (9) | 0.1 | 100 |
|  | 0.01 | 100 |
|  | 0.001 | 100 |
| (1) | 0.1 | 100 |
|  | 0.01 | 100 |
|  | 0.001 | 100 |
| (8) | 0.1 | 100 |
|  | 0.01 | 100 |
|  | 0.001 | 100 |
| (2) | 0.1 | 100 |
|  | 0.01 | 100 |
|  | 0.001 | 100 |
| (19) | 0.1 | 100 |
|  | 0.01 | 100 |
|  | 0.001 | 95 |
| (21) | 0.1 | 100 |
|  | 0.01 | 100 |
|  | 0.001 | 100 |
| (23) | 0.1 | 100 |
|  | 0.01 | 100 |
|  | 0.001 | 98 |
| (17) | 0.1 | 100 |
|  | 0.01 | 100 |
|  | 0.001 | 100 |
| (18) | 0.1 | 100 |
|  | 0.01 | 100 |
|  | 0.001 | 100 |
| (40) | 0.1 | 100 |
|  | 0.01 | 100 |
|  | 0.001 | 98 |
| (41) | 0.1 | 100 |
|  | 0.01 | 100 |
|  | 0.001 | 100 |
| (42) | 0.1 | 100 |
|  | 0.01 | 100 |
|  | 0.001 | 80 |
| (27) | 0.1 | 100 |
|  | 0.01 | 100 |
|  | 0.001 | 95 |

EXAMPLE 2

Laphygma test

Solvent: 3 parts by weight of acetone
Emulsifier: 1 part by weight of alkylaryl polyglycol ether To produce a suitable preparation of active compound 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% meant that all the caterpillars had been killed, whereas 0% indicated that no caterpillars had been killed.

The active compounds, the concentrations of the active compound, the evaluation times and the results can be seen from the following table:

TABLE 2

(insects which damage plants)
Laphygma test

| Active compounds | Active compound concentration in % | Degree of destruction in % after 3 days |
| --- | --- | --- |
| (A) | 0.1 | 100 |
|  | 0.01 | 80 |
|  | 0.001 | 0 |
| (D) | 0.1 | 100 |
|  | 0.01 | 95 |
|  | 0.001 | 0 |
| (E) | 0.1 | 100 |
|  | 0.01 | 100 |
|  | 0.001 | 0 |
| (B) | 0.1 | 100 |
|  | 0.01 | 100 |
|  | 0.001 | 0 |
| (16) | 0.1 | 100 |
|  | 0.01 | 100 |
|  | 0.001 | 100 |
| (6) | 0.1 | 100 |
|  | 0.01 | 100 |
|  | 0.001 | 100 |
| (7) | 0.1 | 100 |
|  | 0.01 | 100 |
|  | 0.001 | 100 |
| (1) | 0.1 | 100 |
|  | 0.01 | 100 |
|  | 0.001 | 100 |
| (2) | 0.1 | 100 |
|  | 0.001 | 100 |
|  | 0.001 | 100 |
| (17) | 0.1 | 100 |
|  | 0.01 | 100 |
|  | 0.001 | 100 |
| (18) | 0.1 | 100 |
|  | 0.01 | 100 |
|  | 0.001 | 100 |
| (40) | 0.1 | 100 |
|  | 0.01 | 100 |
|  | 0.001 | 100 |
| (41) | 0.1 | 100 |
|  | 0.01 | 100 |
|  | 0.001 | 100 |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from the following table:

TABLE 3

(mites which damage plants)
Tetranychus test

| Active compounds | Active compound concentration in % | Degree of destruction in % after 2 days |
| --- | --- | --- |
| (B) | 0.1 | 0 |
| (5) | 0.1 | 100 |
| (3) | 0.1 | 100 |
| (14) | 0.1 | 98 |
| (4) | 0.1 | 100 |
| (16) | 0.1 | 99 |
| (10) | 0.1 | 98 |
| (6) | 0.1 | 99 |
| (7) | 0.1 | 100 |
| (15) | 0.1 | 99 |
| (9) | 0.1 | 100 |
| (1) | 0.1 | 100 |
| (8) | 0.1 | 100 |
| (2) | 0.1 | 100 |
| (21) | 0.1 | 100 |
| (18) | 0.1 | 99 |
| (40) | 0.1 | 100 |
| (41) | 0.1 | 99 |
| (42) | 0.1 | 100 |
| (27) | 0.1 | 100 |

EXAMPLE 4

Critical concentration test/soil insects

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (for example mg/l). The soil was filled into pots and the pots were left to stand at room temperature.

After 24 hours the test insects were introduced into the treated soil and after a further 2-7 days the degree of effectiveness of the active compound was determined in % by counting the dead and live test insects. The degree of effectiveness was 100% if all the test insects had been killed and was 0% if exactly as many test insects were still alive as in the case of the control.

The active compounds, amounts used and results can be seen from the table which follows:

TABLE 4

Soil insecticides
*Tenebrio molitor* larvae in the soil

| Active compound | Degree of destruction in % with an active compound concentration of 2,5 ppm |
| --- | --- |
| (D) | 0 |
| (A) | 0 |
| (18) | 100 |

TABLE 4-continued

Soil insecticides
*Tenebrio molitor* larvae in the soil

| Active compound | Degree of destruction in % with an active compound concentration of 2,5 ppm |
|---|---|
| (1) | 100 |

EXAMPLE 5

Critical concentration test/soil insects

Test insect: *Phorbia antiqua* grubs in the soil
Solvent: 3 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

TABLE 5

Soil insecticides
*Phorbia antiqua* grubs in the soil

| Active compound | Degree of destruction in % with an active compound concentration of 2.5 ppm |
|---|---|
| (D) | 0 |
| (A) | 0 |
| (18) | 100 |
| (1) | 100 |
| (6) | 100 |
| (7) | 100 |
| (21) | 100 |
| (15) | 100 |
| (10) | 100 |
| (19) | 100 |
| (3) | 100 |
| (4) | 100 |
| (20) | 100 |

EXAMPLE 6

$LD_{100}$ test

Test insects: *Blatta orientalis*
Solvent: acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per $m^2$ of filter paper varied with the concentration of the solution of active compound. About 25 test insects were then placed in the Petri dish and it was covered with a glass lid.

The condition of the test insects was observed 3 days after the commencement of the experiments. Th destruction, in %, was determined. 100% denoted that all the test insects had been killed; 0% denoted that no test insects had been killed.

The active compounds, the concentrations of the active compounds, the test insects and the results can be seen from the following table:

TABLE 6

$LD_{100}$ test

| Active compounds | Active compound concentrations % strength solution | Destruction in % |
|---|---|---|
| (A) | 0.2 | 0 |
| (B) | 0.2 | 0 |
| (D) | 0.2 | 0 |
| (C) | 0.2 | 0 |
| (18) | 0.2 | 100 |
| (21) | 0.2 | 100 |
| (8) | 0.2 | 100 |
| (17) | 0.2 | 100 |

EXAMPLE 7

$LT_{100}$ test for Diptera

Test insect: *Musca domestica*
Solvent: acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per $m^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

TABLE 7

$LT_{100}$ test for Diptera (*Musca domestica*)

| Active compounds | Active compound concentration of solution in % | $LT_{100}$ |
|---|---|---|
| (D) | 0.2 | 70' |
|  | 0.02 | 6 hours = 0% |

TABLE 7-continued

| | LT₁₀₀ test for Diptera (*Musca domestica*) | |
|---|---|---|
| Active compounds | Active compound concentration of solution in % | LT₁₀₀ |
| (A) | 0.2 | 150' |
| | 0.02 | 6 hours = 0% |
| (18) | 0.2 | 30' |
| | 0.02 | 60' |
| | 0.002 | 6 hours |
| (1) | 0.2 | 80' |
| | 0.02 | 6 hours |
| (6) | 0.2 | 40' |
| | 0.02 | 6 hours = 70% |
| (21) | 0.2 | 30' |
| | 0.02 | 100' |
| (2) | 0.2 | 55' |
| | 0.02 | 6 hours |
| (8) | 0.2 | 55' |
| | 0.02 | 6 hours = 60% |
| (17) | 0.2 | 55' |
| | 0.02 | 90' |
| | 0.002 | 6 hours = 60% |
| (9) | 0.2 | 140' |
| | 0.02 | 160' |

EXAMPLE 8

Aerosol test

Test insects: *Musca domestica* (female) (resistant to phosphoric acid esters)
Solvent: acetone/amount: 2 cm²

To produce a suitable preparation of active compound, 2 mg of active compound were mixed with the stated amount of solvent.

A wire cage containing about 25 test insects was suspended in the middle of a gas-tight glass chamber of size 1 m³. When the chamber had again been closed, 2 ml of the active compound preparation were atomized therein. The condition of the test insects was constantly checked from outside, through the glass walls, and the time required for 95% destruction of the insects was determined.

The active compounds, active compound concentrations and times at which 95% destruction was achieved can be seen from the table which follows:

TABLE 8

| | Aersol test | |
|---|---|---|
| Active compounds | Active compound concentrations, mg per m³ of air | LT₉₅ |
| (F) | 2 | 1 hr = 50% |
| (B) | 2 | 1 hr = 20% |
| (18) | 2 | 19' 30" |

EXAMPLE 9

Tick test

Solvent: 35 parts by weight of ethylene glycol monomethyl ether
35 parts by weight of nonylphenol polycol ether To prepare a suitable formulation, three parts by weight of active compound were mixed seven parts of the above-mentioned solvent/emulsifier mixture and the emulsion concentrate thus obtained was diluted with water to the particular concentration desired.

Adult, fully bloated female ticks of the species *Boophilus microplus* (resistant) were dipped for one minute into these active compound preparations. After dipping, 10 female specimens were transferred into each of several Petri dishes, the bottom of each dish being lined with a filter disc of corresponding size.

After 10 days, the activity of the active compound preparation was determined by examining the inhibition of the laying of eggs, as compared to untreated control ticks. This action was expressed as a percentage, with 100% denoting that eggs were no longer laid and 0% denoting that the ticks laid normal amounts of eggs.

The active compound examined, the concentration tested, the parasites tested and the findings obtained can be seen from the table which follows.

TABLE 9

| | Tick Test (*Boophilus microplus*, Biarra strain, resistant) | |
|---|---|---|
| Active compound | Active compound concentration in ppm | Destructive action in % |
| (E) | 10,000 | 0 |
| (21) | 10,000 | 100 |
| | 1,000 | 100 |
| | 100 | 0 |

The process of the present invention is illustrated by the following preparative examples.

EXAMPLE 10

The phenoxybenzyl alcohols required as starting compounds could be prepared as follows:

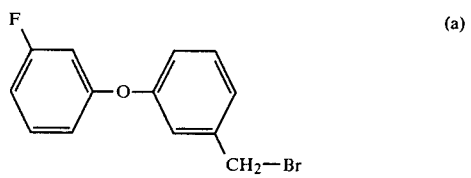
(a)

90 g (0.445 mol) of 3-(3-fluorophenoxy)-toluene were dissolved in 300 ml of anhydrous carbon tetrachloride and heated under reflux together with 79.3 g of N-bromosuccinimide. After reaching 70° C., 5 g of azodiisobutyronitrile were added. After about 10–20 minutes the reaction commenced, with evolution of heat, and after the exothermic reaction had subsided the mixture was heated for a further 4 hours under reflux. The reaction batch was then cooled to 10° C., the succinimide was filtered off and the carbon tetrachloride was distilled of in vacuo. The oil which remained was distilled at 143°-150° C./1 mm Hg. 72.9 g (58.2% of theory) of 3-(3-fluorophenoxy)-benzyl bromide were obtained.

The following could be prepared analogously:

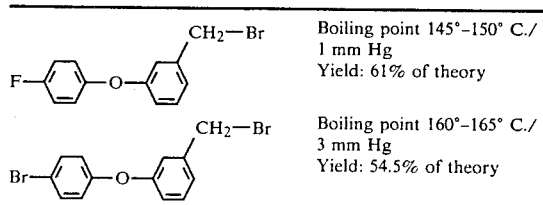

Boiling point 145°-150° C./ 1 mm Hg
Yield: 61% of theory

Boiling point 160°-165° C./ 3 mm Hg
Yield: 54.5% of theory

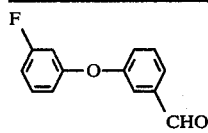
(b)

48 g (0.17 mol) of 3-(3-fluorophenoxy)-benzyl bromide and 47.8 g of hexamethylenetetramine in 250 ml of methylene chloride were heated for 3 hours under reflux. The mixture was then cooled to 5°-10° C. and the resulting precipitate was filtered off. The latter was washed with 100 ml of methylene chloride, suction-dried and then heated, in 100 ml of 50% strength aqueous acetic acid, for 5 hours under reflux. Thereafter, 25 ml of concentrated hydrochloric acid were added and the mixture was again heated for 30 minutes under reflux and then cooled to 10°-20° C. 200 ml of water were added to the reaction mixture, the batch was extracted twice with 150 ml of ether at a time and the combined ether phases were then washed with sodium bicarbonate solution and dried over sodium sulfate. The ether was distilled off in vacuo. 3-(3-Fluorophenoxy)-benzaldehyde, of boiling point 142°-148° C./1 mm Hg, was obtained in 31% yield.

The following could be prepared analogously:

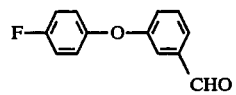   Melting point 48° C.
Yield: 62% of theory

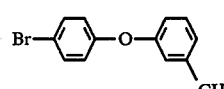   Refractive index $n_D^{22}$: 1.6109
Yield: 67% of theory

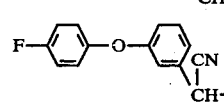   (c-1)

21.6 g (0.1 mol) of 3-(4-fluorophenoxy)-benzaldehyde were dissolved in 25 ml of glacial acetic acid and 10.2 g of sodium cyanide, dissolved in 25 ml of water, were added dropwise at 5° C., while stirring. The reaction mixture was then stirred for 8 hours at 20° C., poured into 100 ml of water and extracted with 200 ml of ether, and the ether phase was separated off. To remove the glacial acetic acid, the ether phase was washed with dilute sodium bicarbonate solution and then dried over sodium sulfate. After distilling off the ether in vacuo, 17 g (70% of theory) of 3-(4-fluorophenoxy)-α-cyanobenzyl alcohol having a refractive index $n_D^{23}$ of 1.5643 were obtained.

The following could be prepared analogously:

   Refractive index $n_D^{21}$: 1.5561
Yield: 93% of theory

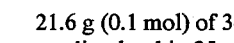   Refractive index $n_D^{22}$: 1.5973
Yield: 88% of theory

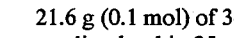   (c-2)

14 g (0.13 mol) of bromoethane were slowly added dropwise, while stirring, to 2.4 g (0.1 mol) of magnesium filings in 70 ml of anhydrous tetrahydrofuran at 30°-40° C. and the mixture was then stirred for a further 30 minutes at 50° C. The Grignard solution thus prepared was transferred into a dropping funnel under nitrogen and was added dropwise to a saturated solution of acetylene in 40 ml of anhydrous tetrahydrofuran, the solution having been saturated at 20° C. During the addition further acetylene was passed in continuously, and this was continued for a further 30-45 minutes after the end of the dropwise addition. 10.8 g (0.05 mol) of 3-(4-fluorophenoxy)-benzaldehyde, dissolved in 50 ml of absolute tetrahydrofuran, were added dropwise to the suspension of ethynyl magnesium bromide, thus prepared, at 25°-30° C., and the mixture was then warmed to 40° C. for 4 hours. Thereafter the reaction batch was cooled to 10° C. and poured into 500 ml of ice-water, and the resulting precipitate was dissolved by adding concentrated hydrochloric acid. The mixture was then extracted twice with 150 ml of ether at a time, the ether phases were dried over sodium sulfate and the ether was then distilled off in vacuo. 7.3 g (61% of theory) of 3-(4-fluorophenoxy)-α-ethynyl-benzyl alcohol were obtained as a yellow oil of boiling point 160°-180° C./3 mm Hg.

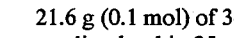   (c-3)

54 g (0.25 mol) of 3-(4-fluorophenoxy)-benzaldehyde, dissolved in 50 ml of dry ether, were added dropwise, with good stirring, to 3.8 g of lithium aluminum hydride in 100 ml of anhydrous ether at the boil. The reaction batch was then stirred further for 10 hours at 22° C. and thereafter cooled to 0° C., and ice-water was added dropwise, while stirring, until no further evolution of hydrogen could be observed. The resulting precipitate was dissolved by adding 10%-strength sulfuric acid and the reaction mixture was then extracted twice with 100 ml of ether at a time. The ether phases were separated off, washed with saturated sodium chloride solution and dried over sodium sulfate. After distilling off the ether in vacuo, 41.5 g (76.1% of theory) of 3-(4-fluorophenoxy)-benzyl alcohol having a refractive index $n_D^{21}$ of 1.5725 were obtained.

The following could be prepared analogously:

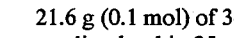   Yield: 76% of theory

EXAMPLE 11

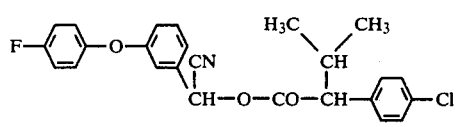
(1)

8 g (0.033 mol) of 3-(4-fluorophenoxy)-α-cyanobenzyl alcohol and 7.6 g (0.033 mol) of α-isopropyl-4-chlorophenylacetic acid chloride were dissolved in 150 ml of anhydrous toluene and 2.64 g (0.033 mol) of pyridine, dissolved in 50 ml of toluene, were added dropwise at 25°–30° C., while stirring. Stirring was then continued for a further 3 hours at 25° C. The reaction mixture was poured into 150 ml of water and the organic phase was separated off and washed further with 100 ml of water. The toluene phase was then dried over sodium sulfate and the solvent was distilled off in a water-pump vacuum. The last remnants of solvent were removed by brief slight distillation under a pressure of 1 mm Hg at a bath temperature of 60° C. 13.2 g (91% of theory) of 3'-(4-fluorophenoxy)-α'-cyanobenzyl-α-isopropyl-4-chlorophenyl acetate were obtained as a yellow oil having a refractive index $n_D^{25}$ of 1.5549.

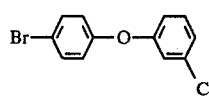

Yield: 71 % of theory
Refractive index $n_D^{24}$: 1.6009

EXAMPLE 12

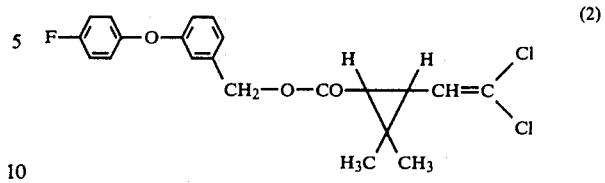
(2)

7.6 g (0.035 mol) of 3-(4-fluorophenoxy)-benzyl alcohol and 7.95 g (0.035 mol) of 2,2-dimethyl-3-(2,2-dichlorovinyl)cyclopropanecarboxylic acid chloride were dissolved in 100 ml of anhydrous toluene and 2.8 g (0.035 mol) of pyridine, dissolved in 50 ml of toluene, were added dropwise at 25°–30° C., while stirring. Stirring was then continued for a further 3 hours at 25° C. The reaction mixture was then poured into 150 ml of water, and the toluene phase was separated off and washed further with 100 ml of water. The organic phase was dried over sodium sulfate and the toluene was then distilled off in a water-pump vacuum. The last remnants of solvent were removed by slight distillation under a pressure of 1 mm Hg and at a bath temperature of 60° C. 11 g (77% of theory) of 3'-(4-fluorophenoxy)-benzyl-2,2-dimethyl-3-(2,2-dichlorovinyl)-cyclopropanecarboxylate were obtained as a yellow oil having a refractive index $n_D^{22}$ of 1.5559.

The following compounds of the general formula

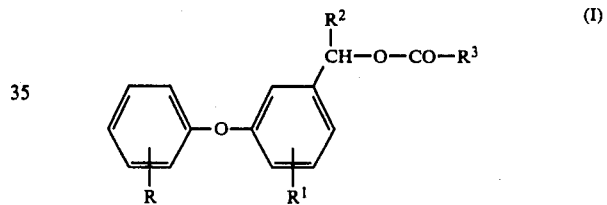
(I)

could be prepared analogously:

TABLE 10

| Compound No. | R | $R^1$ | $R^2$ | $R^3$ | Physical data (refractive index) | Yield (% of theory) |
|---|---|---|---|---|---|---|
| 3 | 4-F | H | H | H₃C\\_CH_/CH₃ —CH—⟨⟩—Cl | $n_D^{24}$:1.5585 | 85 |
| 4 | 4-F | H | H | H₃C\\_CH_/CH₃ —CH—⟨⟩—Br | $n_D^{24}$:1.5668 | 70 |
| 5 | 4-F | H | H | H₃C\\_CH_/CH₃ —CH—⟨⟩—CH₃ | $n_D^{24}$:1.5499 | 93 |
| 6 | 4-F | H | CN | H₃C\\_CH_/CH₃ —CH—⟨⟩—CH₃ | $n_D^{24}$:1.5452 | 83 |
| 7 | 4-F | H | CN | H₃C\\_CH_/CH₃ —CH—⟨⟩—Br | $n_D^{24}$:1.5658 | 71 |

TABLE 10-continued

| Compound No. | R | $R^1$ | $R^2$ | $R^3$ | Physical data (refractive index) | Yield (% of theory) |
|---|---|---|---|---|---|---|
| 8 | 4-F | H | CN | -CH(CH(CH₃)₂)-C₆H₄-4-F | $n_D^{22}$:1.5447 | 81 |
| 9 | 3-F | H | CN | -CH(CH(CH₃)₂)-C₆H₄-4-Cl | $n_D^{22}$:1.5510 | 81 |
| 10 | 4-Br | H | CN | -CH(CH(CH₃)₂)-C₆H₄-4-CH₃ | $n_D^{24}$:1.5688 | 96 |
| 11 | 4-Br | H | H | -CH(CH(CH₃)₂)-C₆H₄-4-Cl | $n_D^{24}$:1.5778 | 95 |
| 12 | 4-Br | H | H | -CH(CH(CH₃)₂)-C₆H₄-4-Br | $n_D^{24}$:1.5880 | 87 |
| 13 | 4-Br | H | H | -CH(CH(CH₃)₂)-C₆H₄-4-CH₃ | $n_D^{24}$:1.5707 | 91 |
| 14 | 4-Br | H | CN | -CH(CH(CH₃)₂)-C₆H₄-4-Br | $n_D^{24}$:1.5840 | 77 |
| 15 | 4-Br | H | CN | -CH(CH(CH₃)₂)-C₆H₄-4-Cl | $n_D^{24}$:1.5757 | 85 |
| 16 | 4-F | H | CN | -CH(CH(CH₃)₂)-(3,4-methylenedioxyphenyl) | $n_D^{23}$:1.5574 | 68 |
| 17 | 3-F | H | CN | -C(C(CH₃)₂H)(H)-CH=CCl₂ | $n_D^{22}$:1.5513 | 88 |
| 18 | 4-F | H | CN | -C(C(CH₃)₂H)(H)-CH=CCl₂ | $n_D^{25}$:1.5505 | 89 |
| 19 | 4-Br | H | CN | -C(C(CH₃)₂H)(H)-CH=C(CH₃)₂ | $n_D^{24}$:1.5578 | 77 |
| 21 | 4-F | H | CN | -C(C(CH₃)₂H)(H)-CH=C(CH₃)₂ | $n_D^{24}$:1.5348 | 78 |
| 23 | 4-Br | H | CN | -C(C(CH₃)₂H)(H)-CH=CCl₂ | $n_D^{22}$:1.5596 | 88 |

TABLE 10-continued

| Compound No. | R | R¹ | R² | R³ | Physical data (refractive index) | Yield (% of theory) |
|---|---|---|---|---|---|---|
| 24 | 4-F | H | H | -CH(CH(CH₃)₂)-C₆H₄-F | $n_D^{27}$:1.5449 | 76 |
| 25 | 4-F | H | H | -CH(CH(CH₃)₂)-C₆H₄-CH(CH₃)₂ | | |
| 26 | 4-F | H | H | -CH(CH(CH₃)₂)-C₆H₄-SCH₃ | | |
| 27 | 4-F | H | C≡CH | -CH(CH(CH₃)₂)-C₆H₄-Cl | $n_D^{24}$:1.5613 | 83 |
| 28 | 4-F | H | C≡CH | -CH(CH(CH₃)₂)-C₆H₄-CH₃ | | |
| 29 | 3-F | H | C≡CH | -CH(CH(CH₃)₂)-C₆H₄-Cl | | |
| 30 | 3-F | H | C≡CH | -CH(CH(CH₃)₂)-C₆H₄-OCH₃ | | |
| 31 | 4-F | H | CN | -CH(CH(CH₃)₂)-C₆H₄-CH(CH₃)₂ | | |
| 32 | 4-F | H | CN | -CH(CH(CH₃)₂)-C₆H₄-OCH₃ | | |
| 33 | 3-F | H | CN | -CH(CH(CH₃)₂)-C₆H₁₀-CH₃ | | |
| 34 | 3-F | H | CN | -CH(CH(CH₃)₂)-C₆H₄-NO₂ | | |
| 35 | 3-F | H | CN | -CH(CH(CH₃)₂)-C₆H₄-CH(CH₃)₂ | | |
| 36 | 3-F | H | CN | -CH(CH(CH₃)₂)-C₆H₄-OCH₃ | | |
| 37 | 4-F | H | H | -CH(CH(CH₃)₂)-C₆H₃(O-O) (methylenedioxy) | | |

TABLE 10-continued

| Compound No. | R | R¹ | R² | R³ | Physical data (refractive index) | Yield (% of theory) |
|---|---|---|---|---|---|---|
| 38 | 3-F | H | CN | (CH₃)₂C-CH=CBr₂ | | |
| 39 | 4-F | H | H | (CH₃)₂C-CH=CBr₂ | | |
| 40 | 4-F | H | C≡CH | (CH₃)₂C-CH=CCl₂ | $n_D^{24}$:1.5573 | 77 |
| 41 | 4-F | H | CN | (CH₃)₂C-CH=CBr₂ | $n_D^{24}$:1.5630 | 84 |
| 42 | 4-F | H | CN | -CH-CH(CH₃)₂ with phenyl | $n_D^{22}$:1.5519 | 83 |
| 43 | 3-F | H | H | (CH₃)₂C-CH=CBr₂ | | |
| 44 | 3-F | H | H | (CH₃)₂C-CH=CCl₂ | | |
| 45 | 3-F | H | C≡CH | (CH₃)₂C-CH=CCl₂ | | |
| 46 | 3-F | H | C≡CH | (CH₃)₂C-CH=C(CH₃)₂ | | |
| 47 | 4-F | H | C≡CH | (CH₃)₂C-CH=C(CH₃)₂ | | |
| 48 | 2-F | H | CN | (CH₃)₂C-CH=CCl₂ | $n_D^{22}$:1.5564 | 84 |
| 49 | 2-F | H | CN | -CH(CH(CH₃)₂)-C₆H₄-Cl | $n_D^{22}$:1.5571 | 74 |

It will be appreciated that the instant specification and examples are set forth by way of illustration and not limitation, and that various modifications and changes may be made without departing from the spirit and scope of the present invention.

What is claimed is:

1. A 3-phenoxybenzyl alcohol carboxylic acid ester of the formula

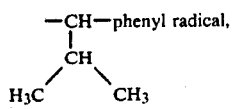
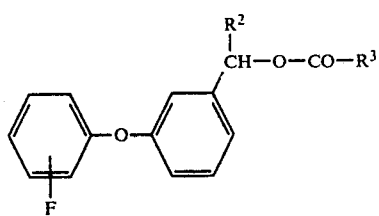

in which

R² represents hydrogen cyano or ethynyl and

R³ represents the

—CH—phenyl radical,
|
CH
/  \
H₃C   CH₃ wherein the phenyl ring can optionally carry one or more substituents selected independently from halogen, alkyl, alkylthio and alkoxy with in each case 1 to 4 carbon atoms, nitro and methylenedioxy.

2. An ester according to claim 1, in which

R³ represents the α-isopropylbenzyl radical, the ring of which can optionally carry one or more substituents selected independently from fluorine, chlorine, bromine, methylenedioxy, methoxy, ethoxy, methylthio, ethylthio, straight-chain or branched alkyl with 1 to 3 carbon atoms and nitro.

3. The compound according to claim 1, wherein such compound is 3'-(4-fluorophenoxy)-α'-cyanobenzyl-α-isopropyl-4-chlorophenyl acetate of the formula

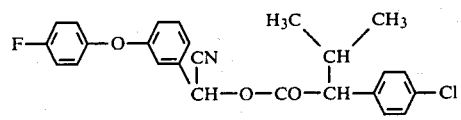

4. The compound according to claim 1, wherein such compound is 3'-(3-fluorophenoxy)-α'-cyanobenzyl-α-isopropyl-4-chlorophenyl acetate of the formula

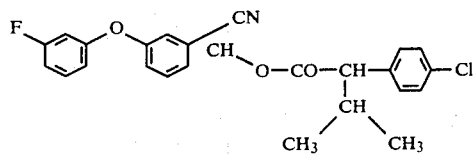

5. An arthropodicidal composition containing as active ingredient an arthropodicidally effective amount of a compound according to claim 1 in admixture with a diluent.

6. A method of combating arthropods which comprises applying to the arthropods, or to a habitat thereof, an arthropodicidally effective amount of a compound according to claim 1.

7. The method according to claim 7, wherein there is applied to a domesticated animal 3'-(4-fluorophenoxy)-α'-cyanobenzyl-α-isopropyl-4-chlorophenyl acetate or, 3'-(3-fluorophenoxy)-α'-cyanobenzyl-α-isopropyl-4-chlorophenyl acetate.

* * * * *